United States Patent [19]

Fixel

[11] Patent Number: 5,087,260
[45] Date of Patent: Feb. 11, 1992

[54] TOTAL FEMORAL HIP SYSTEM

[76] Inventor: Irving E. Fixel, 111 N. 31st Ave., Hollywood, Fla. 33021

[21] Appl. No.: 407,563

[22] Filed: Sep. 15, 1989

[51] Int. Cl.$^5$ .............................................. A61F 5/04
[52] U.S. Cl. ....................................... 606/65; 606/66; 606/69; 606/71
[58] Field of Search ........ 128/92 YU, 92 ZW, 92 YS, 128/92 YP, 92 YF, 92 Z, 92 YZ, 92 YE, 92 YK, 92 R; 606/64, 65, 66, 67, 68, 88, 89, 91

[56] References Cited

U.S. PATENT DOCUMENTS

| | | | |
|---|---|---|---|
| 2,397,545 | 4/1946 | Hardinge | 128/92 YV |
| 2,801,631 | 8/1957 | Charnley | 128/92 YV |
| 3,308,812 | 3/1967 | Gidlund | 128/92 YK |
| 3,489,143 | 1/1970 | Halloran | 128/92 YK |
| 4,120,298 | 10/1978 | Fixel | 128/92 YP |
| 4,129,903 | 12/1978 | Huggler | 606/67 |
| 4,438,762 | 3/1984 | Kyle | 128/92 YV |
| 4,612,920 | 9/1986 | Lower | 128/92 YK |
| 4,628,923 | 12/1986 | Medoff | 128/92 YV |
| 4,657,001 | 4/1987 | Fixel | 128/92 YK |
| 4,776,329 | 10/1988 | Treharne | 128/92 YV |

FOREIGN PATENT DOCUMENTS 3722852 1/1989 Fed. Rep. of Germany ........ 606/66

OTHER PUBLICATIONS

The Cementless Fixation of Hip Endoprostheses, Edited E. Morscher, Springer-Verlag, Berlin, Heidelberg, N.Y. Tokyo 1984.
Free-Lock System by Zimmer, Warsaw, Indiana 46580 entitled "Keyless Insertion and the Option to Key ... In a Single System" booklet.
Free-Lock System by Zimmer, Warsaw, Indiana 46580 entitled "Surgical Technique" booklet.

*Primary Examiner*—Robert A. Hafer
*Assistant Examiner*—Michael Brown
*Attorney, Agent, or Firm*—Richard M. Saccocio

[57] ABSTRACT

Combination apparatus for a total hip replacement or compression and fixation of the femoral head to a femur is provided. A compression plate is provided with a strut member extending between the barrel of the plate and the lower portion of the plate to significantly reinforce the connection of the barrel to the plate. The barrel is alternatively utilized with a compression screw apparatus or total hip replacement apparatus.

9 Claims, 1 Drawing Sheet

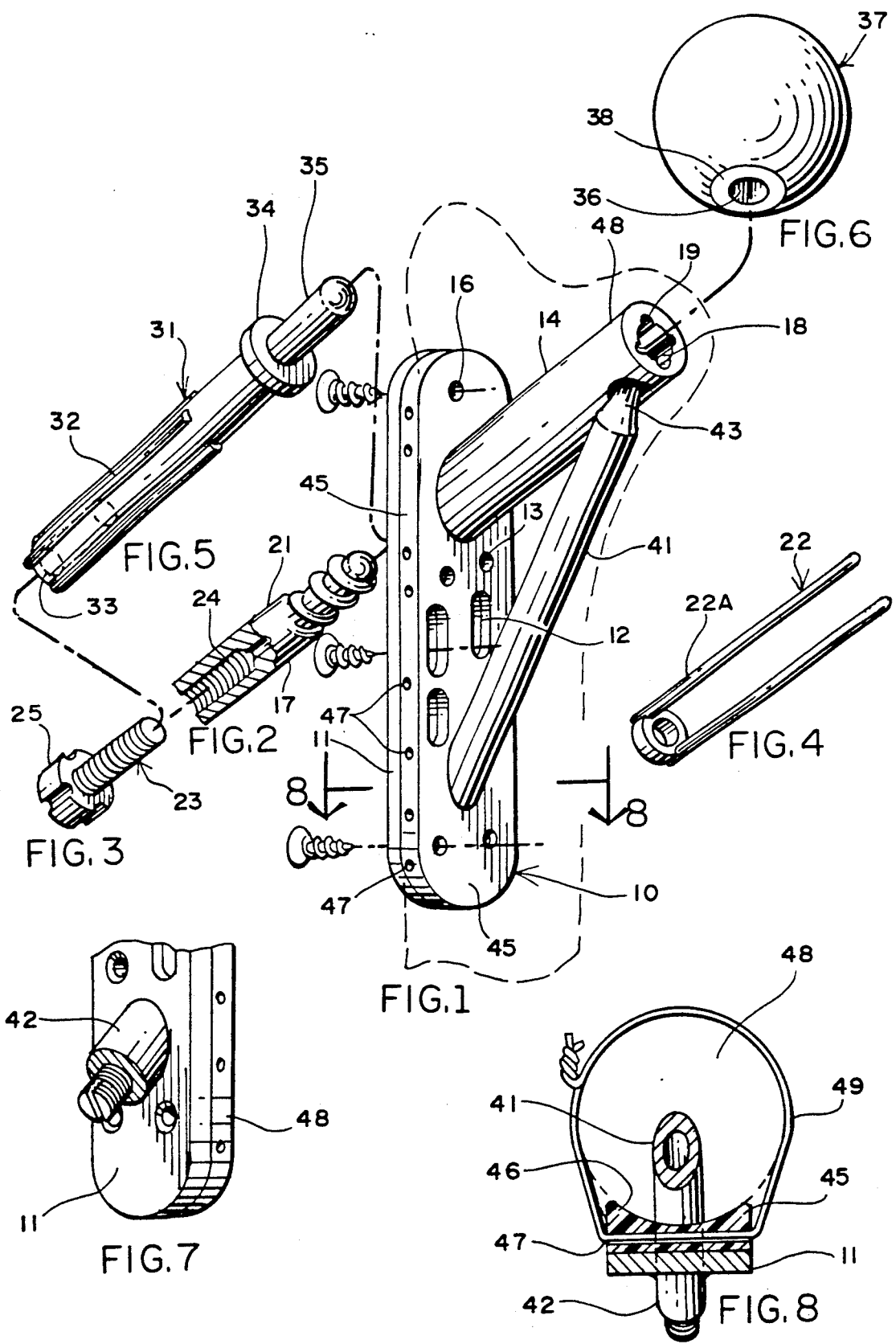

TOTAL FEMORAL HIP SYSTEM

BACKGROUND OF THE INVENTION

1. Field of the Invention

This invention pertains in general to the field of hip bone fixation and hip bone replacement devices and in particular to the field of combination apparatus for replacing the femoral head, reattaching a femoral head, and for fixing and compressing intra-trochanteric and sub-trochanteric fractures of the hip bone.

2. Description of the Prior Art

In the prior art, a device known as a compression hip screw, such as that described in my U.S. Pat. No. 4,657,001, issued Apr. 14, 1987, entitled Antirotational Hip Screw, is typically used for operative reduction and internal fixation of a femoral head or neck fracture of the hip bone. In general, these devices comprise a compression plate with a barrel attached thereto and extending therefrom at an angle of approximately 135°, and a lag screw. The compression plate typically attaches to the outside surface of the femur at the upper end thereof by ordinary screws. The barrel portion within which fits the lag screw, extends through a hole in the neck of the femur and into the head thereof. The lag screw compresses the fracture between the neck and the head, thereby allowing the same to permanently re-attach itself. The barrel attachment to the compression plate must offset the moment load applied to the femur as a result of force downward on the femoral head, and, therefore, is the one "weak link" of these prior art devices. The use of these prior art devices has been successful and substantially trouble-free. Patients having this type of apparatus used to join a broken head from the neck of a femur have been known to be as physically active after the operation as before the operation.

In the prior art, the device most commonly used to replace a femoral head which has become non-functional, comprises an implantable prothesis which includes a one-piece replacement head and femoral neck attached to a relatively large stem, the latter of which fits within a large hole prepared axially in the femoral bone through the upper end thereof. In the early prior art, the stems were cemented within the femoral cavity by the use of a plastic cement. Typically, the cement deteriorates with age, and due to the constant cyclic loading applied to the stem of the prosthesis by the action of simple walking, causes the cement to fracture and break loose from the femoral cavity, thereby requiring another operation to re-fix the prosthesis. Due to the soft nature of the femur and the generally advanced age of the patients needing this type of implant, it is sometimes difficult if not impossible to adequately re-fix the stem of the femoral process within the femoral cavity. When this condition occurs, the patient is often times restricted to the use of wheelchair.

Due to the many problems associated with cementing a femoral hip prothesis within the femur, a cementless type of implant has recently emerged and has been quickly accepted by the orthopedic community as the replacement for the cemented type of hip prothesis. The cementless type of hip prosthesis includes a porous surface over the length of the stem such that natural occurring bone growth after surgery grows into the porous surface of the stem, thereby firmly fixing, at least in theory, the femoral stem within the femoral cavity. The use of this cementless type of device requires that the patient be relatively immobile for a number of weeks following the surgery in order to allow the bone growth to occur and thereafter restrict his physical activities until a firm bond is created. These periods of time may involve a full twelve months.

The cementless type of femoral hip prosthesis is now in wide spread use today. One problem associated with this cementless type of hip prosthesis is the relatively long recovery period of time mentioned above. Another problem is the need for bone growth to occur to firmly fix the implanted prosthesis. Sometimes, the patient's physical activities, however restricted, still prevent firm bonding of the prosthesis to the femur. Another problem is that it is very difficult to remove a firmly bonded prosthesis should a failure of the prosthesis occur after surgery. The removal problem, although very significant, has assumed secondary status because of the relatively good adhesion provided by the bone growing into the porous surface of the stem portion. Notwithstanding the advantages of the cementless type of hip prosthesis as compared to the cemented type of hip prosthesis, there are occasions, all to frequently, where the implant of the hip prosthesis fails requiring another operation to attempt to fix the same.

In either of the two types of hip prosthesis of the prior art, that is the cemented type and the non-cemented type, the problem still exists where the stem does not adhere to the femoral cavity causing loosening of the prosthesis and subsequent failure of the bone joint. In these instances, it often very difficult to re-insert another femoral hip prosthesis and have the same subsequently firmly affix itself within the femoral cavity.

Accordingly, there still exists a definite need for a total hip arthroplastic prosthesis which does not deteriorate with use and require subsequent replacement.

A primary objective of the present invention is to provide a total hip prosthesis wherein the femoral head of a femur is replaced and which replacement does not become loose during use.

Another object of the present invention is to provide a total hip prosthesis which, if necessary, may be easily removed a number of years following the initial surgery.

Another object of the present invention is to provide a total hip prosthesis which allows a patient to be substantially completely mobile after the operation.

Another object of the present invention is to provide a total hip prosthesis which can also be used to compress and fix fractures of the upper portion of a femur such as a neck break, an intratrochanteric break, and subtrochanteric fractures.

Another object of the present invention is to provide compression hip screw apparatus and total hip replacement apparatus having significantly improved strength characteristics to reduce the moment loads imposed by the offset load applied to the head of the femur which must translate along the neck of the femur and be reacted by the body proper of the femur.

The above-stated objects as well as others objects which although not specifically stated, but are intended to be included within the scope of the present invention, are accomplished by the present invention and will become apparent from the hereinafter set forth Detailed Description of the Invention, Drawings, and the claims appended herewith.

SUMMARY OF THE INVENTION

The present invention accomplishes the above-stated objectives as well as others, and comprises combination hip compression screw apparatus and total hip replacement prosthesis which can also be used to compress and fix fractures of the intratrochanteric and subtrochanteric areas of the femur.

The present inventive apparatus comprises a total femoral hip system having the advantage of a compression screw apparatus and the strength characteristics of the neck portion of a total hip prosthesis. A compression plate is provided which is to be secured to the outside surface of the femur. An extending barrel portion is integrally attached to the compression plate so as to provide significant strength at the juncture of the barrel and the compression plate. The barrel portion is adapted to receive a replacement femoral head such as that typically used with the prior art total hip prosthesis. The barrel portion is also adapted to receive a compression lag screw and antirotational devices which may be used to compress and fix a fracture across the neck of a femur. A uniquely arranged strut member is used to support and give additional strength to the barrel-compression plate connection.

In the event of a fracture of the femoral head across the neck between it and the femur, the present inventive apparatus may be used to compress and fix the same when used as a compression hip screw. If thereafter, the femoral head deteriorates to the point that it needs replacement, the present inventive apparatus may be used as a total hip prosthesis, without relying upon the fixation of a stem to a cavity prepared in the upper portion of the femur. Note, however, that the present inventive apparatus may be initially used as a total hip prosthesis without first being used as a compression hip screw. In the unlikely event that the present inventive device being used as a total hip prosthesis fails, it is still possible to use a prior art device utilizing a prepared cavity in the upper portion of the femur to which a stem may be inserted.

BRIEF DESCRIPTION OF THE DRAWINGS

Various other objects, advantages, and features of the invention will become apparent to those skilled in the art from the following discussion taken in conjunction with the following drawings, in which:

FIG. 1 presents in isometric view of the inventive total femoral hip system;

FIG. 2 comprises a plan view of a lag screw used with the barrel and plate apparatus of FIG. 1;

FIG. 3 is a plan view of a compression screw used with the lag screw of FIG. 2 and the barrel and plate of FIG. 1;

FIG. 4 comprises one type of key apparatus which may be used prevent rotation of the lag screw of FIG. 2 within the barrel of FIG. 1;

FIG. 5 comprises the shank portion of a total hip replacement prosthesis used with the barrel and plate of FIG. 1;

FIG. 6 comprises ball apparatus utilized with the shank of FIG. 5 to replace the deteriorated head of a patient's femur;

FIG. 7 is a partial isometric view of the outside portion of the plate of FIG. 1 illustrating a method of securing the strut to the compression plate; and, FIG. 8 comprises a cross-sectional view of the compression plate of FIG. 1 taken through the line 8—8 thereof.

DESCRIPTION OF THE PREFERRED EMBODIMENTS

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various figures are designated by the same reference numerals.

Referring now to FIGS. 1 through 4 of the drawings, there is shown therein the present inventive apparatus 10 being utilized as a compression hip screw to aid in the compression and fixation of a head of a head of a femur which is broken across the neck between the head and the femur itself. The compression plate 11 comprises an elongated member having a plurality of slots 12 and holes 13 therethrough which may be used to secure the compression plate 11 to the outside and upper surface of a person's femur bone. Integrally attached to said compression plate 11 is a barrel 14. Barrel 14 is integrally attached to compression plate 11 whereby both the barrel and the compression plate 14 and 11, respectively, may be made from one piece of metal. Typically, the metal used for barrel 14 and compression plate 11 is titanium. A generous radius 15 is provided at the junction of the barrel 14 and the compression plate 11 so as to minimize any stress concentration at this area and yet provide significant strength at the junction. Above and below the barrel 14 and through the compression plate 11 lies a pair of holes 16 which alternatively may be used for pins to fix the position of the broken femoral head prior to application of the lag screw 17 within the barrel 14 and into the interior portion of the femoral head.

Holes 16 may also be used for the insertion of connecting screws to connect the compression plate to the outside of the femur. In this regard, holes 16 each comprise a chamfered or counterdrilled hole to accommodate the head of a screw. Or, hole 16 may first be used with antirotational pins and thereafter be used with fixation screws.

Internally, barrel 14 is provided with a through hole 18 and a plurality of grooves 19 extending the length of barrel 14. Grooves 19 in conjunction with grooves 21 on lag screw 17 and further in conjunction with key apparatus 22 having one or more keys 22a attached thereto to prevent rotation of the lag screw 17 after a femoral head has been reattached to the neck of a femur. Accordingly, the grooves 21 in lag screws 17 and 19 within barrel 14 are to be aligned with each other after a femoral head has been compressed and fixed by lag screw 17 within and extending from barrel 14. Once the one or more pairs of grooves 21 and 19 are aligned, one or more keys 22a can be used to firmly lock the lag screw 17 with respect to the barrel 14. It is to be noted, however, that lag screw 17 may still slide axially within barrel 14 even with one or more keys 22a connecting there respective grooves 21 and 19.

The compression screw 23 is adapted to be inserted within opening 24 in the aft end of lag screw 17, and threaded thereto. The head 25 of compression screw 23 fits against a seat within compression plate 11 which is machined concentric with opening 18 through barrel 14 so that the tightening rotation of screw 23 causes lag screw 17 to move further within barrel 14 and such that a fracture between the neck and the head of a femur is compressed.

The barrel 14, lag screw 17, compression screw 23, and the one or more keys 22a, utilized within the present invention may also comprise the apparatus shown and claimed in my U.S. Pat. No. 4,657,001, issued Apr. 14, 1987, which patent is incorporated by reference as if fully set forth herein.

Reference is now made to FIGS. 5 and 6 of the drawings. A shank 31 comprises an elongated rod having one or more flutes 32 axially extending along a portion of the length of shank 31. Flutes 32 coincide with the grooves 19 within barrel 14. Accordingly, shank 31 may be fitted within the opening 18 of barrel 14 and such that the flutes 32 align and fit within the grooves 19 within the opening 18 of barrel 14.

An opening 32 in the aft end of shank 31 is threaded and allows the attachment thereto of screw 23 to firmly lock shank 31 within barrel 14. The forward end of shank 31 includes a flange 34 and an extending rod member 35. Shank 31, flange 34, and extending rod member 35 are preferably all made from a single piece of material, such as titanium. Extending rod portion 35 fits within opening 36 of replacement head member 37 such that head 37 may be firmly attached to shank 31 but yet may rotate with respect thereto. Head 37, of course, is a replacement head for a deteriorated femoral head of a person's hip joint. A flat surface 38 provided at the base of head 37 provides a bearing surface of head 37 with respect to flange 34 of shank 31.

A reinforcing strut member 41 is provided between the lower end of compression plate 11 and the forward or extending end 48 of barrel 14. As shown in FIG. 7, strut 41 is threadingly attached within a boss member 42 extending at an angle from the outside surface of compression plate 11. The tip or upper end 43 of strut 41 may be tapered to fit within a similarly tapered opening 44 in the bottom of extending end 48 of barrel 14. Opening 44 may be immediately adjacent to the entrance to hole 18 so as to allow strut member 41 to act as an effective brace. Strut 41 may be applied after compression plate 11 has been attached to the patient and either of the apparatus disclosed and shown within FIGS. 2 through 4 or FIGS. 5 to 6 are utilized with compression plate 11. Accordingly, the attachment of strut 41 may be considered to be a final procedure in the application of the present inventive apparatus 10 to the femur of a person. In accordance with FIG. 1, it is seen that strut member 41 significantly increases the strength of the barrel 14 to plate 11 connection to resist the cyclic loads applied by the force of a person walking to the head of the femur and thence along barrel 14 to the connection 15 between valve 14 and plate 11. Strut 41 may be sufficiently thin and the spacing between adjacent parallel rows of holes 13 and slots 12 are such that strut 41 does not cause interference with screws applied to either of the rows of slots 12 and holes 13.

Compression plate 11 further includes a backing plate member 45 which may be made from plastic and attached to compression plate 11 such as by gluing. Backing plate 45 includes a curved surface 46 to coincide with the transverse curvature of a person's femur 48 so as to rest securely there against. Backing plate 45 further includes a plurality of holes 47 extending transversely along the width of compression plate 18. Holes 47 provide an opening through compression plate 11 which allows the insertion of a length of wire 49 which may be wrapped around the bone through the holes 47 so as to temporarily secure compression plate 11 to the femur in the initial stages of the operation, or alternatively to piece together to the main portion of the femur loose and broken off portions of the same.

While the invention has been described, disclosed, illustrated and shown in certain terms or certain embodiments or modifications which it has assumed in practice, the scope of the invention is not intended to be nor should it be deemed to be limited thereby and such other modifications or embodiments as may be suggested by the teachings herein are particularly reserved especially as they fall within the scope of the breadth and scope of the claims here appended.

I claim as my invention:

1. Combination hip compression screw and total hip replacement apparatus adapted to be secured to a person's femur comprising:

an elongated plate having a barrel member attached at one end of said plate and extending cantileverly therefrom;

said plate including means for attaching said plate to said femur; and a brace for structurally supporting the cantilever attachment of said barrel to said plate said brace having a first end fixedly attached to said plate and a second end disengaged from, and in supporting contact to said extending barrel member.

2. The apparatus of claim 1, wherein said brace means comprises an elongated rod extending at an angle from said plate attached at one end to said plate and in supporting contact at a second end with the extending end of said barrel.

3. The apparatus of claim 1, including a lag screw fitted within an opening through said barrel and said plate.

4. The apparatus of claim 3, including screw means for axially securing said lag screw within said opening in said barrel and plate.

5. The apparatus of claim 1, including a shank member fitted within said barrel, and a femoral head replacement member rotatingly attached to said shank member.

6. The apparatus of claim 5, including screw means for axially securing said shank member within said barrel.

7. The apparatus of claim 1, including a backing member attached to said plate, said backing member having one or more holes thereacross the width thereof.

8. The apparatus of claim 7, adapted to be attached to a femur, further comprising a wire threaded through said one or more holes thereacross and secured to said femur.

9. The apparatus of claim 1, wherein said plate includes a plurality of axially spaced slots therethrough.

* * * * *